(12) United States Patent
Krabben et al.

(10) Patent No.: US 10,550,396 B2
(45) Date of Patent: Feb. 4, 2020

(54) DELETION MUTATIONS

(71) Applicant: GREEN BIOLOGICS LIMITED, Abingdon, Oxfordshire (GB)

(72) Inventors: Preben Krabben, Didcot (GB); Elizabeth Jenkinson, Abingdon (GB)

(73) Assignee: GREEN BIOLOGICS LIMITED, Abingdon, Oxfordshire (GB)

( * ) Notice: Subject to any disclaimer, the term of this patent is extended or adjusted under 35 U.S.C. 154(b) by 34 days.

(21) Appl. No.: 15/304,467

(22) PCT Filed: Apr. 16, 2015

(86) PCT No.: PCT/GB2015/051152
§ 371 (c)(1),
(2) Date: Oct. 14, 2016

(87) PCT Pub. No.: WO2015/159086
PCT Pub. Date: Oct. 22, 2015

(65) Prior Publication Data
US 2017/0037415 A1 Feb. 9, 2017

(30) Foreign Application Priority Data
Apr. 17, 2014 (GB) .................................. 1406968.6

(51) Int. Cl.
*C12N 15/74* (2006.01)
(52) U.S. Cl.
CPC .................................. *C12N 15/74* (2013.01)
(58) Field of Classification Search
None
See application file for complete search history.

(56) References Cited

U.S. PATENT DOCUMENTS

| | | | |
|---|---|---|---|
| 8,420,782 B2 | 4/2013 | Bonas et al. | |
| 2011/0027835 A1 | 2/2011 | Heap et al. | |
| 2011/0119779 A1 | 5/2011 | Shizuya et al. | |
| 2012/0190116 A1 | 7/2012 | Soucaille et al. | |
| 2012/0202251 A1 | 8/2012 | Cornish et al. | |
| 2012/0301964 A1 | 11/2012 | Tracy et al. | |
| 2014/0141516 A1 | 5/2014 | Tracy et al. | |

FOREIGN PATENT DOCUMENTS

| | | |
|---|---|---|
| NO | 2002/0047 | 7/2003 |
| WO | WO 2003/056936 | 7/2003 |
| WO | WO 2007/148091 | 12/2007 |
| WO | WO 2008/040387 | 4/2008 |
| WO | WO 2009/101400 | 8/2009 |
| WO | WO 2013/133882 | 9/2013 |
| WO | WO 2013/141680 | 9/2013 |
| WO | WO 2013/142578 | 9/2013 |
| WO | WO 2014/093595 | 6/2014 |
| WO | WO 2014/143381 | 9/2014 |
| WO | WO 2014/191518 | 12/2014 |
| WO | WO 2015/040402 | 3/2015 |
| WO | WO 2015/123339 | 8/2015 |

OTHER PUBLICATIONS

Al-Hinai, M., Fast, A. and Papoutsakis, E. (2012) 'Novel system for efficient isolation of Clostridium double-crossover allelic exchange mutants enabling markerless chromosomal gene deletions and DNA integration', Applied and environmental microbiology, 78(22), pp. 8112-8121.
Altschul, S., Madden, T., Schäffer, A., Zhang, J., Miller, W. and Lipman, D. (1997) 'Gapped BLAST and PSI-BLAST: A new generation of protein database search programs', Nucleic acids research, 25(17), pp. 3389-3402.
Bahl, H. and Dürre, P. (eds.) (2001) Clostridia: Biotechnology and Medical Applications. Wiley-Blackwell.
Barrangou, R. and Marraffini, L. (2014) 'CRISPR-Cas systems: Prokaryotes upgrade to adaptive immunity', Molecular cell., 54(2), pp. 234-244.
Brown, S., Nagaraju, S., Utturkar, S., Tissera, D., Segovia, S., Mitchell, W., Land, M., Dassanayake, A. and Köpke, M. (2014) 'Comparison of single-molecule sequencing and hybrid approaches for finishing the genome of Clostridium autoethanogenum and analysis of CRISPR systems in industrial relevant Clostridia', Biotechnology for biofuels, 7.
Cartman, S., Kelly, M., Heeg, D., Heap, J. and Minton, N. (2012) 'Precise manipulation of the Clostridium difficile chromosome reveals a lack of association between the tcdC genotype and toxin production', Applied and environmental microbiology, 78(13), pp. 4683-4690.
Cobb, R., Wang, Y. and Zhao, H. (2014) 'High-efficiency multiplex genome editing of *Streptomyces* species using an engineered CRISPR/Cas system', ACS synthetic biology, 4(6), pp. 723-728.
Cong, L., Ran, F., Cox, D., Lin, S., Barretto, R., Habib, N., Hsu, P., Wu, X., Jiang, W., Marraffini, L. and Zhang, F. (2013) 'Multiplex genome engineering using CRISPR/Cas systems' and Supplementary Materials, Science (New York, N.Y.)., 339(6121), pp. 819-823.
Constantino PNAS 100, 15748-15753 (2003).
DiCarlo, J., Norville, J., Mali, P., Rios, X., Aach, J. and Church, G. (2013) 'Genome engineering in *Saccharomyces cerevisiae* using CRISPR-Cas systems', Nucleic acids research., 41(7), pp. 4336-4343.
Didelot, X. and Falush, D. (2007) 'Inference of bacterial Microevolution using Multilocus sequence data', Genetics, 175(3).
Doudna, J. and Charpentier, E. (2014) 'Genome editing. The new frontier of genome engineering with CRISPR-Cas9', Science (New York, N.Y.), 346(6213).

(Continued)

*Primary Examiner* — Nancy A Treptow
(74) *Attorney, Agent, or Firm* — Knobbe Martens Olson & Bear LLP

(57) ABSTRACT

The present invention relates to a process for removing genetic material from a bacterial cell, specifically producing deletions in bacterial genomes or eliminating endogenous bacterial plasmids. In particular, the process relates to the transformation of bacterial cells with one or more Deletion Vectors, wherein the Deletion Vectors are capable of directing production of two or more crRNAs which target two or more PAM/Protospacers within the genomes of the bacteria within the population or within endogenous bacterial plasmids.

14 Claims, 3 Drawing Sheets
Specification includes a Sequence Listing.

(56) References Cited

OTHER PUBLICATIONS

Fujii, W., Onuma, A., Sugiura, K. and Naito, K. (2014) 'Efficient generation of genome-modified mice via offset-nicking by CRISPR/Cas system', Biochemical and biophysical research communications., 445(4), pp. 791-794.
Garneau, J.E., Dupuis, M.E., Villion, M., Romero, D.A., Barrangou, R., Boyaval, P., Fremaux, C., Horvath, P., Magadan, A.H. and Moineau, S. (2010) 'The CRISPR/Cas bacterial immune system cleaves bacteriophage and plasmid DNA', Nature, 468(7320), pp. 67-71. doi: 10.1038/nature09523.
Gomaa, A.A., Klumpe, H.E., Luo, M.L., Selle, K. and Barrangou, R. (2014) 'Programmable removal of bacterial strains by use of genome-targeting CRISPR-Cas systems', mBio, 5(1), pp. 13-928. doi: 10.1128/mBio.00928-13.
Gratz, S., Wildonger, J., Harrison, M. and O'Connor-Giles, K. (2013) 'CRISPR/Cas9-mediated genome engineering and the promise of designer flies on demand', Fly., 7(4), pp. 249-255.
Grissa, I., Vergnaud, G. and Pourcel, C. (2007) 'CRISPRFinder: A web tool to identify clustered regularly interspaced short palindromic repeats', Nucleic acids research, 35.
Heap, J.T., Cartman, S.T., Pennington, O.J., Cooksley, C.M., Scott, J.C., Blount, B., Burns, D. and Minton, N.P. (2009) 'Development of Genetic Knock-out Systems for Clostridia', in Bruggemann, H. and Gottschalk, G. (eds.) Clostridia: Molecular biology in the Post-genomic Era.
Heap, J.T., Pennington, O.J., Cartman, S.T. and Minton, N.P. (2009) 'A modular system for Clostridium shuttle plasmids', Journal of Microbiological Methods, 78(1), pp. 79-85. doi: 10.1016/j.mimet. 2009.05.004.
Horii, T., Morita, S., Kimura, M., Kobayashi, R., Tamura, D., Takahashi, R., Kimura, H., Suetake, I., Ohata, H., Okamoto, K., Tajima, S., Ochiya, T., Abe, Y. and Hatada, I. (2013) 'Genome engineering of mammalian haploid embryonic stem cells using the Cas9/RNA system', PeerJ, 1.
Hwang, W.Y., Fu, Y., Reyon, D., Maeder, M.L., Tsai, S.Q., Sander, J.D., Peterson, R.T., Yeh, J.J. and Joung, K.J. (2013) 'Efficient in vivo genome editing using RNA-Guided Nucleases', Nature Biotechnology, 31(3).
Jiang, W., Bikard, D., Cox, D., Zhang, F. and Marraffini, L. (2013) 'RNA-guided editing of bacterial genomes using CRISPR-Cas systems' and Supplementary Materials, Nature biotechnology, 31(3), pp. 233-239.
Kiro, R., Shitrit, D. and Qimron, U. (2014) 'Efficient engineering of a bacteriophage genome using the type I-E CRISPR-Cas system', RNA biology, 11(1), pp. 42-44.
Lee, J., Jang, Y. Lee, J. Papoutsakis, E. and Lee, S. (2009) 'Metabolic engineering of Clostridium acetobutylicum M5 for highly selective butanol production', Biotechnology journal, 4(10), pp. 1432-1440.
Ma, B., Tromp, J. and Li, M. (2002) 'PatternHunter: Faster and more sensitive homology search', Bioinformatics (Oxford, England), 18(3), pp. 440-445.
Maiden, M., Bygraves, J., Feil, E., Morelli, G., Russell, J., Urwin, R., Zhang, Q., Zhou, J., Zurth, K., Caugant, D., Feavers, I., Achtman, M. and Spratt, B. (1998) 'Multilocus sequence typing: A portable approach to the identification of clones within populations of pathogenic microorganisms', Proceedings of the National Academy of Sciences of the United States of America, 95(6), pp. 3140-3145.
Makarova, K., Haft, D., Barrangou, R., Brouns, S., Charpentier, E., Horvath, P., Moineau, S., Mojica, F., Wolf, Y., Yakunin, A., der, van and Koonin, E. (2011) 'Evolution and classification of the CRISPR-Cas systems', Nature reviews Microbiology, 9(6), pp. 467-477.
Mali, P., Yang, L., Esvelt, K., Aach, J., Guell, M., DiCarlo, J., Norville, J. and Church, G. (2013) 'RNA-guided human genome engineering via Cas9', Science (New York, N.Y.), 339(6121), pp. 823-826.
Nair, R.V. and Papoutsakis, E.T. (1994) 'Expression of plasmid-encoded aad in Clostridium acetobutylicum M5 restores vigorous butanol production', Journal of Bacteriology, 176(18), pp. 5843-5846. doi: 10.1128/jb.176.18.5843-5846.1994.
Ran, F.A., Hsu, P.D., Wright, J., Agarwala, V., Scott, D.A. and Zhang, F. (2013) 'Genome engineering using the CRISPR-Cas9 system', Nature Protocols, 8(11), pp. 2281-2308. doi: 10.1038/nprot. 2013.143.
Ran, F., Hsu, P., Lin, C., Gootenberg, J., Konermann, S., Trevino, A., Scott, D., Inoue, A., Matoba, S. and Zhang, Y. (2013) 'Double nicking by RNA-guided CRISPR Cas9 for enhanced genome editing specificity', Cell., 154(6), pp. 1380-1389.
Richter, H., Randau, L. and Plagens, A. (2013) 'Exploiting CRISPR/Cas: Interference mechanisms and applications', International Journal of Molecular Sciences, 14(7).
Richter, H., Zoephel, J., Schermuly, J., Maticzka, D., Backofen, R. and Randau, L. (2012) 'Characterization of CRISPR RNA processing in Clostridium thermocellum and Methanococcus maripaludis', Nucleic acids research., 40(19), pp. 9887-9896.
Rocha, E.P.C., Cornet, E. and Michel, B. (2005) 'Comparative and evolutionary analysis of the bacterial homologous recombination systems', PLoS Genetics, 1(2).
Sillers, R., Chow, A., Tracy, B. and Papoutsakis, E. (2008) 'Metabolic engineering of the non-sporulating, non-solventogenic Clostridium acetobutylicum strain M5 to produce butanol without acetone demonstrate the robustness of the acid-formation pathways and the importance of the electron balance', Metabolic engineering, 10(6), pp. 321-332.
Upadhyay, S., Kumar, J., Alok, A. and Tuli, R. (2013) 'RNA-guided genome editing for target gene mutations in wheat', G3 (Bethesda, Md.), 3(12), pp. 2233-2238.
Vercoe, R., Chang, J., Dy, R., Taylor, C., Gristwood, T., Clulow, J., Richter, C., Przybilski, R., Pitman, A. and Fineran, P. (2013) 'Cytotoxic chromosomal targeting by CRISPR/Cas systems can reshape bacterial genomes and expel or remodel pathogenicity islands', PLoS genetics., 9(4).
Vos, M. and Didelot, X. (2008) 'A comparison of homologous recombination rates in bacteria and archaea', The ISME journal, 3(2), pp. 199-208.
Wang, Y., Zhang, Z., Seo, S., Choi, K., Lu, T., Jin, Y. and Blaschek, H. (2015) 'Markerless chromosomal gene deletion in Clostridium beijerinckii using CRISPR/Cas9 system', Journal of biotechnology, 200, pp. 1-5.
Westra, E., Staals, R., Gort, G., Høgh, S., Neumann, S., de, la, Fineran, P. and Brouns, S. (2013) 'CRISPR-Cas systems preferentially target the leading regions of MOBF conjugative plasmids', RNA biology, 10(5), pp. 749-761.
Xu, T., Li, Y., Shi, Z., Hemme, C., Zhu, Y., Nostrand, V., He, Z. and Zhou, J. (2015) 'Efficient genome editing in Clostridium cellulolyticum via CRISPR-Cas9 Nickase' and Supplementary Materials, Applied and environmental microbiology, 81(13), pp. 4423-4431.
Zhong, J., Karberg, M. and Lambowitz, A. (2003) 'Targeted and random bacterial gene disruption using a group II intron (targetron) vector containing a retrotransposition-activated selectable marker', Nucleic acids research, 31(6), pp. 1656-1664.
Li et al., CRISPR/Cas: A novel way of RNA-guided genome editing, Chinese Academy of Sciences, Beijing, China, 2013, 35(11): 1265-1273.
Sontheimer et al., Microbiology: Slicer for DNA, Nature, 2010, 468(732): 45-56.
Combined Search and Examination Report dated Feb. 1, 2016 for Application No. GB1506469.4.
Examination Report dated Aug. 1, 2016 for Application No. GB1506469. 4.
Combined Search and Examination Report dated Nov. 1, 2016 for Application No. GB1616433.7.
Combined Search and Examination Report dated Nov. 1, 2016 UK Application No. GB1616429.5.
Official Letter dated Sep. 18, 2017 for EP Application No. 15718987. 9.
Official Letter dated Jul. 26, 2018 for EP Application No. 15718987. 9.
Office Action dated Oct. 17, 2018 for U.S. Appl. No. 15/304,483.

(56) References Cited

OTHER PUBLICATIONS

Combined Search and Examination Report dated Feb. 1, 2016 for Application No. GB1506460.3.
Examination Report dated Jul. 1, 2016 for Application No. GB1506460.3.
Official Letter dated Sep. 14, 2017 for EP Application No. 15718988.7.
Official Letter dated Jul. 26, 2018 for EP Application No. 15718988.7.
International Search Report and Written Opinion dated Jun. 26, 2015 for International Application No. PCT/GB2015/051153.
International Search Report and Written Opinion dated Jun. 26, 2015 for International Application No. PCT/GB2015/051152.
Office Action dated in related Chinese patent application No. 201580024688X dated Jan. 9, 2019.
Office Action dated in related Chinese patent application No. 2015800246907 dated Jan. 15, 2019.
JP Official Action dated Apr. 23, 2019 for application No. 2017-505733 with machine translation thereof.
Office Action dated May 24, 2019 in Chinese Patent Application No. 201580024690.7.

Figure 1

SEQ ID NO.

1.  C_saccharoper_N1504         CTTTTAATATATCCATATTGGAATGTAAAT
2.  C_saccharoper_N14_HMT       GTTTTATATTAAC-TATGAGGAATGTAAAT
3.  C_sp_DLVIII                 GTTTTATATTAAC-TATGAGGAATGTAAAT
4.  C_saccharob_NCP258_2        GTTTTATCTTAAC-TA-GAGGAATGTAAAT
5.  C_tyro_ATCC52755_1          GTTGAACCTTAACATGAGATGTATTTAAAT
6.  C_tyro_ATCC52755_2          ATTGAACCTTAACATGAGATGTATTTAAAT
7.  C_saccharob_NCP262_1        GATTAACATTAACATGAGATGTATTTAAAT
8.  C_saccharob_NCP258_1        GTTGAAGATTAACATTATATGTTTTGAAAT
9.  C_saccharob_NCP262_2        GTTGAAGATTAACATTATATGTTTTGAAAT
10. C_pasteurianum_DSM525       GTTGAACCTTAACATAGGATGTATTTAAAT
11. C_autoethanogenum           GTTGAACCTCAACATGAGATGTATTTAAAT

SEQUENCE LISTING

<160> NUMBER OF SEQ ID NOS: 12

<210> SEQ ID NO 1
<211> LENGTH: 30
<212> TYPE: DNA
<213> ORGANISM: Clostridium saccharoperbutylacetonicum

<400> SEQUENCE: 1
cttttaatat atccatattg gaatgtaaat        30

<210> SEQ ID NO 2
<211> LENGTH: 29

<212> TYPE: DNA
<213> ORGANISM: Clostridium saccharoperbutylacetonicum

<400> SEQUENCE: 2
gttttatatt aactatgagg aatgtaaat                                29

<210> SEQ ID NO 3
<211> LENGTH: 29
<212> TYPE: DNA
<213> ORGANISM: Clostridium sp DLVIII

<400> SEQUENCE: 3
gttttatatt aactatgagg aatgtaaat                                29

<210> SEQ ID NO 4
<211> LENGTH: 28
<212> TYPE: DNA
<213> ORGANISM: Clostridium saccharobutylicum

<400> SEQUENCE: 4
gttttatctt aactagagga atgtaaat                                 28

<210> SEQ ID NO 5
<211> LENGTH: 30
<212> TYPE: DNA
<213> ORGANISM: Clostridium tyrobutyricum

<400> SEQUENCE: 5
gttgaacctt aacatgagat gtatttaaat                               30

<210> SEQ ID NO 6
<211> LENGTH: 30
<212> TYPE: DNA
<213> ORGANISM: Clostridium tyrobutyricum

<400> SEQUENCE: 6
attgaacctt aacatgagat gtatttaaat                               30

<210> SEQ ID NO 7
<211> LENGTH: 30
<212> TYPE: DNA
<213> ORGANISM: Clostridium saccharobutylicum

<400> SEQUENCE: 7
gattaacatt aacatgagat gtatttaaat                               30

<210> SEQ ID NO 8
<211> LENGTH: 30
<212> TYPE: DNA
<213> ORGANISM: Clostridium saccharobutylicum

<400> SEQUENCE: 8
gttgaagatt aacattatat gttttgaaat                               30

<210> SEQ ID NO 9
<211> LENGTH: 30
<212> TYPE: DNA
<213> ORGANISM: Clostridium saccharobutylicum

<400> SEQUENCE: 9
gttgaagatt aacattatat gttttgaaat                               30

<210> SEQ ID NO 10

```
<211> LENGTH: 30
<212> TYPE: DNA
<213> ORGANISM: Clostridium pasteurianum

<400> SEQUENCE: 10
gttgaacctt aacataggat gtatttaaat                                    30

<210> SEQ ID NO 11
<211> LENGTH: 30
<212> TYPE: DNA
<213> ORGANISM: Clostridium autoethanogenum

<400> SEQUENCE: 11
gttgaacctc aacatgagat gtatttaaat                                    30

<210> SEQ ID NO 12
<211> LENGTH: 101
<212> TYPE: DNA
<213> ORGANISM: Clostridium saccharoperbutylacetonicum

<400> SEQUENCE: 12
aaaccctatt tccaaaaaaa atgaatgctt ttcatgcttt tttaaaattt cttctatcag   60
cttatttata caaaactctt ctatttttag ctcatatgct t                      101
```

DELETION MUTATIONS

The present invention relates to a process for removing genetic material from a bacterial cell, specifically producing deletions in bacterial genomes or eliminating endogenous bacterial plasmids. In particular, the process relates to the transformation of bacterial cells with one or more Deletion Vectors, wherein the Deletion Vectors are capable of directing production of two or more crRNAs which target two or more PAM/Protospacers within the genomes of the bacteria within the population or within endogenous bacterial plasmids. The bacterial DNA is thereby cleaved in two or more places, and the resulting linearised fragments will be susceptible to degradation by endogenous bacterial mechanisms. If this occurs within the bacterial genome, the two cleaved ends of the major fragment may rejoin, while the minor linear fragment (being shorter) is degraded. If a bacterial plasmid is targeted, even the major fragment will be relatively small and therefore it is likely to be degraded rather than rejoined, resulting in removal of the plasmid from the cell.

Solvent-producing clostridia have been used since the 1910s for the industrial production of acetone, butanol and ethanol. During the 1950s, the establishment of more efficient petrochemical techniques to synthesise these solvents lead to the abandonment of such large-scale bacterial fermentations. However, in the present environment, with increasing pressure for the development of chemicals using sustainable and renewable processes, the interest in clostridial fermentations for the production of solvents is being renewed. This has also been helped by advancements in the biological understanding of these solventogenic clostridia, with the sequencing of several genomes and the use of RNA sequencing and transcriptomics. These areas of research have opened up the possibility of engineering new strains which are capable of over-producing butanol, or removing production of competing by-products, further improving the economics of solventogenic fermentations.

In order to take advantage of this influx of genomic information, there remains a need for quick and effective methods for generating recombinant clostridial and other bacterial strains to facilitate research and understanding, which will lead to the generation of commercially-relevant strains.

It has been traditionally very difficult to generate recombinant clostridial strains. Low transformation efficiencies in combination with low recombination efficiencies have hampered efforts to make stable recombinant strains exhibiting improved solvent-related phenotypes. Over the past few years, technology has been developed that allows insertional inactivation of genes through use of Type II introns, e.g. Targetron (Sigma) and Clostron (e.g. WO 2007/148091), and integration of new pathway genes through the use of 'allele coupled exchange' (ACE, e.g. WO 2009/101400); but deletion of sections of DNA by such methods is laborious and these methods are not applicable to the complete removal of endogenous plasmids.

Allelic exchange methods have been designed in order to generate clostridial strains carrying specific point mutations or in-frame deletions through homologous recombination methods. Due to the difficulties in isolating and selecting for successful recombinant strains, these are generally inefficient, although they can be highly specific (e.g. Cartman et al., Appl. Environ. Microbiol. 78(13), 4683-90 (2012)). Additionally RNA knock-down and interference methods can be useful, as is transposon mutagenesis for generating recombinant strains. However, although these are valuable research tools, these methods target very specific or a narrow range of genes.

In some cases, the deletion of large, regionally targeted but non-specific sections of genomic material is preferred as these methods can be used to generate strains in which complete operons are removed or which can be used to identify essential versus non-essential genetic material. In addition, in some circumstances, it is useful to be able to quickly and efficiently remove endogenous plasmids. Removal of an endogenous plasmid can answer questions regarding essentiality of the plasmid, e.g. a megaplasmid may be essential for cell survival whereas a mini-plasmid may be dispensable. The ability to quickly remove an endogenous plasmid can also be useful when origin incompatibilities interfere with efficient transformation methods thereby making a plasmid-free strain essential for research and exploitation. The loss of these native plasmids 'naturally' may take considerable effort through multiple rounds of passaging and selection.

Genome analysis of resultant plasmid-free or 'deletion carrying' strains may then be used to understand more about microbial physiology which can be potentially linked to substrate uptake mechanisms and production of solvents. For example $C.$ $acetobutylicum$ carries a megaplasmid which encodes both an α-amylase enzyme and the sol operon which is essential for solvent production. In some circumstances this megaplasmid can be lost through strain degeneration. In $C.$ $acetobutylicum$ loss of the megaplasmid provides a starting strain (M5) for manipulating metabolic flux. This can be used to generate strains with altered ratios of acetone:butanol:ethanol solvents, by complementing back only selected genes of the sol operon that were removed with the loss of the plasmid (e.g. Nair et al., J. Bacteriol., 176(18), 5843-6, 1994; Sillers et al., Metab. Eng., 10(6), 321-32, 2008; Lee et al., Biotechnol. J., 4(10), 1432-1440, 2009).

A method which could potentially be used make these genome changes is Transcriptional Activator-Like Endonucleases (TALENs, e.g. U.S. Pat. No. 8,420,782 B2) but the technology has been developed for editing eukaryotic genomes and has not yet been specifically adapted for use in industrially-relevant solventogenic clostridial strains. The need to engineer TALENs for each gene target is costly and time-consuming, and the practicalities of precisely how the technology will work in clostridia all count against it becoming a widely accessible tool in the near future.

Therefore in summary the presently available methods are all complicated, multi-stage and time-intensive procedures for generating highly specific mutations and deletions. In order to enable more rapid screening or investigation of the importance of a variety of chosen genes, operons, and plasmids, a method for simply and rapidly removing fragments of genetic material from within bacterial genomic DNA or from plasmids endogenously present in bacteria in a manner that does not need to be precise would be much more useful.

A novel method has therefore been developed which is based on using the clostridial CRISPR/Cas system. (CRISPR is an acronym for Clustered, Regularly Interspaced, Short, Palindromic Repeats.) These systems are usually described as 'prokaryotic adaptive immune systems' and are the means by which a bacterial or archaeal cell can protect itself from invading DNA, usually phage or plasmid DNA.

Cells with a CRISPR/Cas system are able to selectively integrate short fragments from 'invading' DNA into the Cas gene cluster. Each fragment is called a 'Spacer' and is flanked by direct repeats. If the cell encounters the same invading DNA again, it will recognise it as hostile and will destroy it by cleaving it with the Cas endonuclease.

The sequence that the CRISPR/Cas system recognises in the invading DNA is called the 'Protospacer' and has identity to the Spacer copy in the genome. In order to make sure that the cell does not accidently attack the genomic copy of the Spacer, the Protospacer in Cas I or Cas II systems must have a short sequence associated with it called the PAM sequence. The PAM sequence may be up- or down-stream of the Protospacer sequence depending on the type of system. If it is not present or is mutated in any way, the invading DNA will no longer be recognised by the cell and it will not be destroyed.

The PAM sequence associated with cas9 from *Streptococcus pyogenes* is well known (Jiang et al., Nature Biotech. (March 2013), vol. 31, no. 3, pp. 233-239); however, the PAM associated with clostridial systems has not previously been identified.

Not all prokaryotes have CRISPR/Cas gene homologues and of those that do they fall into several distinct classes (Makarova et al., Nat. Rev. Microbiol., 9(6), 467-77. 2011). A lot of work has been published on the Type II cas 9 system from *Streptococcus pyogenes* and *Streptococcus pneumoniae* (e.g. Jiang et al., Nature Biotech. (March 2013), vol. 31, no. 3, pp. 233-239). This has been developed into a genome-editing tool for use in eukaryotic cells, which has been used successfully in e.g. yeast (DiCarlo et al., Nucleic Acids Research, 41(7), 4336-4343, 2013), zebrafish (Hwang et al., Nat. Biotechnol., 31(3), 227-9. 2013) and mammalian cells (Ran et al., Nature Protocols, 8, 2281-2308, 2013).

In eukaryotes, dsDNA breaks generated by CRISPR/Cas systems can be used to generate deletions and other INDELs (INSertions and DELetions in DNA) to effectively knock out virtually any gene, because of the presence of nonhomologous end joining (NHEJ) pathways in the eukaryote cells. However, most bacteria lack these non-homologous end joining (NHEJ) repair mechanisms, with Cas9 cleavage of genomic sequences believed to lead only to cell death, rather than generation of gene deletions. This was summarised in a review by Barrangou and Marraffini, Molecular Cell, 54(2), 234-244, 2014.

A new process has now been developed which enables the production of deletions in bacterial genomes in a quick and efficient single-step process.

This new process can also be used to remove target endogenous plasmids (including megaplasmids) from bacteria. By targeting two or more locations within the plasmid sequence with the Deletion Vector, the system should cleave the plasmid into two or more linear fragments which should be susceptible to destruction by native cell mechanisms. Given the relatively small size of a plasmid compared to a typical genome, complete degradation of the latter is more likely to occur before rejoing can take place, resulting in loss of the plasmid This could be used to determine if endogenous (mega)plasmids are essential for host survival, and may provide insight into the benefits or metabolic burden of the plasmid to the host cell. In practice, the minimum number of cut sites required to eliminate an endogenous plasmid is likely to be dependent on the size of the target plasmid, as all of the resulting fragments should be sufficiently small that they are degraded rather than rejoined.

In one embodiment, therefore, the invention provides a process for producing a deletion in a bacterial genome, wherein the bacteria comprise a CRISPR/Cas system, the process comprising the steps:
(a) transforming a population of bacteria with one or more Deletion Vectors, wherein the Deletion Vector(s) are capable of directing production of first and second crRNAs which target first and second PAM/Protospacers within the genomes of the bacteria within the population;
(b) culturing the population of bacteria under conditions whereby the first and second crRNAs are produced, wherein they target the first and second PAM/Protospacers, and wherein the first and second crRNAs promote a dual cleavage of the genome in one or more bacteria within the population, and wherein the two cleaved ends of the bacterial genomic DNA rejoin; and
(c) isolating one or more bacteria whose genomes comprise a deletion in the bacterial genomic DNA between the first and second PAM/Protospacers.

In step (c), the deletion in the bacterial genomic DNA preferably comprises at least the region including and between the first and second PAM/Protospacers.

In some embodiments, one Deletion Vector is capable of directing production of both the first and second crRNAs which target first and second PAM/Protospacers within the genomes of the bacteria within the population.

Preferably the Deletion Vector comprises first and second Cas Spacer Elements, flanked by Cas Direct Repeat Elements.

The first and second CRISPR Spacers may be in a single Cas array or in separate Cas arrays within the Deletion Vectors.

In this embodiment, the Deletion Vector preferably comprises:
(i) a Cas Leader Element,
(ii) a first Cas Direct Repeat Element,
(iii) a first Cas Spacer Element which is capable of directing production of the first crRNA,
(iv) a second Cas Direct Repeat Element,
(v) a second Cas Spacer Element which is capable of directing production of the second crRNA, and
(vi) a third Cas Direct Repeat Element.

Alternatively, the Deletion Vector preferably comprises two arrays, the first array comprising:
(i) a first Cas Leader Element,
(ii) a first Cas Direct Repeat Element,
(iii) a first Cas Spacer Element which is capable of directing production of the first crRNA, and
(iv) a second Cas Direct Repeat Element,
and the second array comprising:
(v) a second Cas Leader Sequence,
(vi) a third Cas Direct Repeat Element,
(vii) a second Cas Spacer Element which is capable of directing production of the second crRNA, and
(viii) a fourth Cas Direct Repeat Element.

In other embodiments, a first Deletion Vector is capable of directing production of the first crRNA which targets the first PAM/Protospacers within the genomes of the bacteria within the population; and a second Deletion Vector is capable of directing production of the second crRNA which targets the second PAM/Protospacers within the genomes of the bacteria within the population.

In this embodiment, the first Deletion Vector preferably comprises:
(i) a first Cas Leader Element,
(ii) a first Cas Direct Repeat Element, (iii) a first Cas Spacer Element which is capable of directing production of the first crRNA,
(iv) a second Cas Direct Repeat Element,
and/or the Second Deletion Vector preferably comprises:
(v) a second Cas Leader Element,
(vi) a third Cas Direct Repeat Element,
(vii) a second Cas Spacer Element which is capable of directing production of the second crRNA,
(viii) a fourth Cas Direct Repeat Element.

In a further embodiment, the invention provides a process for producing a rearrangement in a bacterial genome, wherein the bacteria comprise a CRISPR/Cas system, the process comprising the steps:
(a) transforming a population of bacteria with one or more Deletion Vectors, wherein the Deletion Vector(s) are capable of directing production of first and second crRNAs which target first and second PAM/Protospacers within the genomes of the bacteria within the population;
(b) culturing the population of bacteria under conditions whereby the first and second crRNAs are produced, wherein they target the first and second PAM/Protospacers, and wherein the first and second crRNAs promote a dual cleavage of the genome in one or more bacteria within the population; and
(c) isolating one or more bacteria whose genomes comprise a rearrangement in the bacterial genomic DNA compared to control non-transformed bacteria.

In another embodiment, the invention provides a process for removing or deleting DNA from an endogenous plasmid in a bacterium (which is likely to result in a loss of the plasmid), wherein the bacteria comprise a CRISPR/Cas system, the process comprising the steps:
(a) transforming a population of bacteria with one or more Deletion Vectors, wherein the Deletion Vector(s) are capable of directing production of two or more crRNAs which target two or more PAM/Protospacers within the target plasmids in the bacteria within the population;
(b) culturing the population of bacteria under conditions whereby the two or more crRNAs are produced and wherein the two or more crRNAs target the one or more PAM/Protospacers, and wherein the two or more crRNAs promote the cleavage of the target plasmids at two or more locations to produce linearised DNA fragments in two or more bacteria within the population, and wherein the linearised fragments are subject to degradation by endogenous cell mechanisms; and
(c) isolating one or more bacteria who lack the target plasmid.

Preferably, the linearised fragments are subject to degradation by endogenous cell mechanisms before the (inefficient) end rejoining processes are able to repair the plasmid.

The bacteria in the population of bacteria must have a CRISPR/Cas system. This CRISPR/Cas system will be one which is capable of cleaving the chromosomal DNA or other target DNA, e.g. target plasmid, preferably endogenous plasmid of the bacteria using the first and second crRNAs or the two or more crRNAs.

It will be accepted that there may, in some cases, be contamination within bacterial populations. As used herein, the term "population of bacteria" refers primarily to the bacteria which it is desired to transform with the Deletion Vector.

Preferably, the CRISPR/Cas system is a Type I CRISPR/Cas system.

The bacteria in the population may have an endogenous CRISPR/Cas system or the CRISPR/Cas system may be heterologous. For example, a heterologous CRISPR/Cas system may be plasmid-based.

Preferably, the CRISPR/Cas system is an endogenous CRISPR/Cas system, i.e. it is present in the wild-type bacteria. In some embodiments of the invention, the CRISPR/Cas system is not a plasmid-based system.

The bacteria in the population may, for example, be Gram-positive or Gram-negative bacteria. Preferably the bacteria are Gram-positive.

In some embodiments, the bacteria are spore-forming bacteria. In other embodiments, the bacteria are saccharolytic bacteria.

The bacteria may be aerobic or anaerobic bacteria. Preferably, the bacteria are anaerobic bacteria. The bacteria may be thermophilic bacteria.

In yet other embodiments, the bacteria are able to convert a substrate into RCOOH, for example, into acetate and/or butyrate. In this context, R is an aliphatic C1-C5, preferably C1-3, alkyl or alkenyl group. The bacteria may also be able to convert the RCOOH into a solvent, preferably into one or more of acetone, ethanol and/or butanol.

In other embodiments, the bacteria are solvent-producing bacteria. As used herein, the term "solvent-producing" means that the bacteria are those which are capable of producing a solvent, preferably a solvent such as acetone, ethanol, propanol and/or butanol. In certain particularly preferred embodiments, the bacteria are capable of producing ethanol, acetone and butanol. Preferably, the bacteria are butanol-producing bacteria or butanol-tolerant bacteria.

In some preferred embodiments, the bacteria are of the genus *Clostridium*. Preferred *Clostridium* species include *C. acetobutylicum, C. arbusti, C. aurantibutyricum, C. beijerinckii, C. cellulovorans, C. cellulolyticum, C. thermocellum, C. thermobutyricum, C. pasteurianurn, C. kluyveri, C. novyi, C. saccharobutylicum, C. thermosuccinogenes, C. thermopalmarium, C. saccharolyticum, C. saccharoperbutylacetonicum, C. tyrobutyricum, C. tetanomorphum, C. magnum, C. ljungdahlii, C. autoethanogenum, C. butyricum, C. puniceum, C. diolis, C. homopropionicum* and *C. roseum*.

In some preferred embodiments of the invention, the bacteria are *C. saccharoperbutylacetonicum* strain N1, e.g. N1-4. In other embodiments of the invention, the bacteria are *C. saccharoperbutylacetonicum* N1-4 (HMT). In yet other embodiments of the invention, the host cell is *C. saccharoperbutylacetonicum* N1-504.

In other preferred embodiments, the bacteria are *C. pasteurianum* (e.g. DSM 525), *C. tyrobutyricum* (e.g. ATCC 52755), or *C. saccharobutylicum* (e.g. NCP 258 and NCP 262) or *Clostridium* sp. DL-VIII.

In other preferred embodiments, the bacteria are of the genus *Bacillus*. In other preferred embodiments, the bacteria are of the order Actinomycetales. In other embodiments, the bacteria are preferably not *Streptococcus* or *E. coli*.

The bacteria are preferably ones which have an endogenous end-joining enzyme or mechanism. In other embodiments, the bacteria are ones which have an heterologous end-joining enzyme or pathway.

The target plasmid may be an endogenous plasmid (which occurs naturally in the bacteria in question).

The core region of bacterial DNA (genomic or plasmid) to be deleted is flanked by two CRISPR PAM/Protospacers which are capable of being recognised by the bacteria's CRISPR/Cas system.

A PAM/Protospacer is a sequence in the bacterial genome or target plasmid that includes a functional combination of a PAM sequence and a Protospacer. Each PAM/Protospacer sequence is capable of being recognised by the CRISPR/Cas system that is being used and, upon production of the appropriate crRNA, it will be cleaved by the CRISPR/Cas system.

As used herein, the term "functional CRISPR/PAM Protospacer" means a CRISPR PAM/Protospacer which is capable of being recognised by a crRNA which recognises a CRISPR/PAM Protospacer in the bacterial genome or target plasmid. In some cases, a single mutation (e.g. in the PAM sequence) may be enough to render the CRISPR/PAM Protospacer non-functional.

PAM is an abbreviation for Protospacer-Adjacent Motif. PAM Elements are capable of being recognised by the bacterial CRISPR/Cas system. PAM Elements are generally 3-6 nucleotides long and are specific to each bacterial species.

The orientation of the PAM Element with respect to the Protospacer in the bacterial genome or target plasmid is important. In some bacterial species, the PAM Element is generally found at or near the 5' end of the Protospacer; in other species, the PAM Element is generally found at or near the 3' end of the Protospacer.

The PAM Element may be on either strand of the bacterial genome or target plasmid but the sequence chosen as the Cas Spacer Element should be on the same DNA strand as the PAM Element (so that the PAM Element and Protospacer are directly adjacent).

Some studies have found that almost any mutation in the PAM Element eliminates recognition by the CRISPR/Cas system (e.g. Jiang et al., Nature Biotech (March 2013), vol. 31, no. 3, pp. 233-239). The PAM/Protospacers must each have a functional PAM Element, in addition to a functional Protospacer. As used herein, the term "functional PAM Element" or "CRISPR PAM Element which is functional in the bacteria" means that the PAM Element is capable of being recognised by the bacteria's endogenous CRISPR/Cas system or, if the bacteria do not have an endogenous CRISPR/Cas system, by the vector-based heterologous CRISPR/Cas system which has been introduced into the bacteria.

More than one sequence might be able to function as the PAM Element in the chosen bacterial species. For example, the I-E CRISPR-Cas system from *Escherichia coil* K-12 is known to have four functional PAM sequences (Gomaa et al. (2014). mBio, 5(1): e00928-13 DOI: 10.1128/mBio.00928-13), and in *C. saccharoperbutylacetoniucm* N1-4 (HMT), at least four effective PAM sequences (CCC, CCT, CCA and CCG) have been identified using the method described in Example 2.

The ability of a PAM Element to function in a particular bacterial species may be tested by transforming the bacteria having a CRISPR/Cas system (either its endogenous CRISPR/Cas system or a heterologous plasmid-derived system) with a plasmid comprising a CRISPR Spacer, and an adjacent test-PAM Element. If the PAM Element is functional in the bacteria, the PAM Element-containing plasmid will be destroyed by the CRISPR/Cas system and the transformation efficiency will be significantly reduced. The concept is illustrated herein in Example 2.

The CRISPR Protospacers are the sequences within the bacterial genome or target plasmid which are targeted by the crRNAs (provided that compatible PAM Elements are also appropriately located).

In step (a) of the process for producing a deletion in a bacterial genome, a population of bacteria are transformed with one or more Deletion Vectors, wherein the Deletion Vector(s) are capable of directing production of first and second crRNAs which target first and second PAM/Protospacers within the genomes of the bacteria within the population.

The aim of this step (a) is to prepare for the production two crRNAs: the first crRNA will bind to the first PAM/Protospacer in the bacterial genome; and the second crRNA will bind to the second PAM/Protospacer in the bacterial genome.

In step (a) of the process for removing a target plasmid in a bacterium, a population of bacteria are transformed with one or more Deletion Vectors, wherein the Deletion Vector(s) are capable of directing production of two or more crRNAs which target two or more PAM/Protospacers within the target plasmids in the bacteria within the population.

The aim of this step (a) is to prepare for the production the two or more crRNAs which will bind to the one or more PAM/Protospacers in the target plasmid.

In the process for removing a target (preferably endogenous) plasmid in a bacterium, the Deletion Vector may be capable of directing production of one, two, three, four, five or more crRNAs. These may target one, two, three, four, five or more PAM/Protospacers within the target plasmids.

As used herein, the term "transformation" and "transforming" refers to any step by which the Deletion Vector(s) are inserted into the bacterial cells. Hence it includes any form of electroporation, conjugation or transfection, inter alia.

The deletion may be in-frame or not in-frame. The PAM/Protospacers will both/all be within the site of the deletion. Preferably, the deletion includes at least part of the PAM or PAM/Protospacer so that the PAM/Protospacer becomes no longer functional (i.e. no longer recognised by the CRISPR/Cas system).

The Deletion Vector is preferably a circular vector.

The Deletion Vector preferably has an Origin Element, most preferably a Gram positive Origin Element (for example "pBP1").

The Deletion Vector may also comprise an appropriate selection marker (e.g. antibiotic resistance gene).

The Deletion Vector does not comprise a CRISPR PAM/Protospacer which is capable of being recognised by a crRNA which recognises the CRISPR/PAM Protospacer in the bacterial genome (or target plasmid).

In the process for producing a deletion in a bacterial genome, step (b) comprises culturing the population of bacteria under conditions whereby the first and second crRNAs are produced, wherein they target the first and second PAM/Protospacers and wherein the first and second crRNAs promote the cleavage of the genome in one or more bacteria within the population, and wherein the two cleaved ends of the bacterial genomic DNA rejoin.

In this step, either both of the CRISPR PAM/Protospacers are removed from the bacterial genome (in the deletion) or both of the CRISPR PAM/Protospacers are rendered incapable of being recognised by crRNAs which recognise the PAM/Protospacers.

In this step, the bacterium's CRISPR/Cas system (either endogenous or heterologous) will cleave the bacterial genomic DNA at a site within the genomic sequence that corresponds to the first PAM/Protospacer and at a site within the genomic sequence that corresponds to the second PAM/Protospacer. Hence the bacterial genome will be cut twice, linearised and a deleted section of DNA will be liberated. The actual sites of cleavage within the first and second PAM/Protospacers, and hence the extent of the deletion, will be dependent on the distance between the two PAM/Protospacers in the genome. It is very possible that the cleaved ends of the genomic DNA will be trimmed back by cellular mechanisms, prior to rejoining. In some cases, the extent of this trimming back may be quite significant, for example resulting in loss of many kb of sequence flanking the pair of PAM/Protospacer. The maximum extent of trimming could be determined by the proximity of essential genes, as trimming back further (into such genes) would not be viable, and will be in competition with process(es) for end rejoining.

In the process for removing a target plasmid in a bacterium, step (b) comprises culturing the population of bacteria under conditions whereby the two or more crRNAs are produced and wherein the two or more crRNAs target the two or more PAM/Protospacers, and wherein the two or more crRNAs promote the cleavage of the target plasmids at two or more locations to produce linearised DNA fragments in one or more bacteria within the population, and wherein the linearised fragments are subject to degradation by endogenous cell mechanisms. In cases where the degradation occurs more quickly than the DNA rejoining, the plasmid will be lost from the cell.

In this step, the target plasmid is cleaved at or near the CRISPR PAM/Protospacers to produce two or more linear fragments of the plasmid. Such fragments may be degraded by host cell mechanisms before the host repair mechanisms are able to rejoin the DNA.

Suitable conditions for culturing the bacteria will be readily known in the art. Such conditions are, for example, described in "Clostridia: Biotechnology and Medical Applications", Eds H. Bahl and P. Dürre, ISBN 3-527-30175-5, especially section 3.4 "Growth conditions and nutritional requirements". Details are also given in Bergey's Manual of Systematic Bacteriology, Volume appropriate to the chosen phylum of bacteria, e.g. Volume Three for the Firmicutes, ISBN 978-0-387-95041-9.

The term "crRNA" means CRISPR RNA. crRNAs are short single-stranded RNA molecules consisting of short Direct Repeat sequences flanking a target Spacer sequence to be cleaved by the CRISPR/Cas system.

The "Cas Leader Element" is a DNA element which is generally found upstream of the first repeat in the Direct Repeat cluster. It helps to promote the production of crRNA, i.e. it functions as a RNA promoter. Numerous Cas Leader sequences have been identified to date and its sequence may readily be established in any particular Cas system. Preferably, the Cas Leader sequence is one which corresponds to the CRISPR/Cas system which is present in the bacterial population which is being transformed.

The Cas Direct Repeat sequences are DNA elements which are recognised by the CRISPR/Cas system which is present in the population of bacteria. These Direct Repeats are generally 25-35 nucleotides in length, more generally about 29 or 30 nucleotides in length.

The Direct Repeats do not need to be of identical sequence (generally a difference of 1-2 nucleotides is tolerated by the Cas protein). The Direct Repeats generally have palindromic regions which are capable of forming hair-pin loops.

The DNA sequence of Direct Repeats which are suitable for any one CRISPR/Cas system may readily be found from any inspection of the CRISPR/Cas direct repeat-Spacer cluster of that system.

The Cas Spacer Element comprises a sequence of 20-50 nucleotides (preferably 30-40, more preferably 36-38 nucleotides) with a high level of sequence identify to the 20-50 nucleotides (preferably 30-40, more preferably 36-38 nucleotides) which are found (preferably immediately) 5' to the PAM Element in the PAM/Protospacer or (preferably immediately) 3' to the PAM Element in the PAM/Protospacer, depending on the preference of the CRISPR/Cas system which is present in the bacterial population of interest.

Preferably, the PAM Elements in the bacterial genome or target plasmids are directly adjacent to the start of the Protospacer sequences (in the bacterial genome).

The degree of sequence identity between the Protospacers in the genomic DNA or target plasmid and the Spacer Element sequences in the Deletion Vector(s) is each preferably at least 80%, more preferably at least 85%, 90%, 95%, 96%, 97%, 98% or 99%, or is 100%.

Preferably, the Cas Spacer sequence is selected such that there is a low probability of interaction with a non-Protospacer Element.

The first and second Cas Spacer Elements bind to the first and second PAM/Protospacers in the bacterial genome.

Similarly, the Cas Spacer Elements bind to corresponding sites in the target plasmid.

The minimum extent of the deletion is defined by the distance between the first and second PAM/Protospacers.

Preferably, this distance is 10 bp-1000 kb, more preferably 100 bp-100 kb, even more preferably 200-500 bp.

The Deletion Vectors may comprise antibiotic-resistance elements or other selection markers, thus allowing the Vectors to be selected for, e.g. in the presence of certain antibiotics, for example chloramphenicol, erythromycin, tetracycline, spectinomycin, streptomycin etc. Preferably, the Deletion Vectors (when more than one are present) comprise antibiotic-resistance elements which allow for their selection on different antibiotics.

Percentage amino acid sequence identities and nucleotide sequence identities may be obtained using the BLAST methods of alignment (Altschul et al. (1997), "Gapped BLAST and PSI-BLAST: a new generation of protein database search programs", Nucleic Acids Res. 25:3389-3402; and http://www.ncbi.nlm.nih.gov/BLAST). Preferably the standard or default alignment parameters are used.

Standard protein-protein BLAST (blastp) may be used for finding similar sequences in protein databases. Like other BLAST programs, blastp is designed to find local regions of similarity. When sequence similarity spans the whole sequence, blastp will also report a global alignment, which is the preferred result for protein identification purposes. Preferably the standard or default alignment parameters are used. In some instances, the "low complexity filter" may be taken off.

BLAST protein searches may also be performed with the BLASTX program, score=50, wordlength=3. To obtain gapped alignments for comparison purposes, Gapped BLAST (in BLAST 2.0) can be utilized as described in Altschul et al. (1997) Nucleic Acids Res. 25: 3389. Alternatively, PSI-BLAST (in BLAST 2.0) can be used to perform an iterated search that detects distant relationships between molecules. (See Altschul et al. (1997) supra). When utilizing BLAST, Gapped BLAST, PSI-BLAST, the default parameters of the respective programs may be used.

With regard to nucleotide sequence comparisons, MEGA-BLAST, discontiguous megablast, and blastn may be used to accomplish this goal. Preferably the standard or default alignment parameters are used. MEGABLAST is specifically designed to efficiently find long alignments between very similar sequences. Discontiguous MEGABLAST may be used to find nucleotide sequences which are similar, but not identical, to the nucleic acids of the invention.

The BLAST nucleotide algorithm finds similar sequences by breaking the query into short subsequences called words. The program identifies the exact matches to the query words first (word hits). The BLAST program then extends these word hits in multiple steps to generate the final gapped alignments. In some embodiments, the BLAST nucleotide searches can be performed with the BLASTN program, score=100, wordlength=12.

One of the important parameters governing the sensitivity of BLAST searches is the word size. The most important reason that blastn is more sensitive than MEGABLAST is that it uses a shorter default word size (11). Because of this, blastn is better than MEGABLAST at finding alignments to related nucleotide sequences from other organisms. The word size is adjustable in blastn and can be reduced from the default value to a minimum of 7 to increase search sensitivity.

A more sensitive search can be achieved by using the newly-introduced discontiguous megablast page (www.ncbi.nlm.nih.gov/Web/Newsltr/FallWinter02/blast-lab.html). This page uses an algorithm which is similar to that reported by Ma et al. (Bioinformatics. 2002 March; 18(3): 440-5). Rather than requiring exact word matches as seeds for alignment extension, discontiguous megablast uses non-contiguous word within a longer window of template. In coding mode, the third base wobbling is taken into consideration by focusing on finding matches at the first and second codon positions while ignoring the mismatches in the third position. Searching in discontiguous MEGABLAST using the same word size is more sensitive and efficient than standard blastn using the same word size. Parameters unique for discontiguous megablast are: word size: 11 or 12; template: 16, 18, or 21; template type: coding (0), non-coding (1), or both (2).

The two cleaved ends of the bacterial genome will be rejoined by bacterial DNA repair mechanisms. (The skilled artisan will readily appreciate that the references herein to "two cleaved ends" refer to the two double-stranded DNA ends of the bacterial genome, which technically comprise four DNA strands.)

Smaller fragments, for example generated from cleavage of megaplasmids or plasmids may not rejoin, but instead be degraded by cellular mechanisms before rejoining can occur.

The deletion will often be a crude deletion, i.e. the deletion will often not be a precise rejoining between the two ends of the bacterial genome which have been cut by the Cas enzyme. For example, the cell repair mechanism may process the cut ends resulting in the deletion of one or potentially many more additional nucleotides. For example, the deletion may comprise a deletion of 1-5 kb, 5-10 kb, 10-30 kb, 30-50 kb or 50-100 kb DNA on one or both sides of the region of DNA flanked by the first and second PAM/Protospacer sites.

In the process for producing a deletion in a bacterial genome, step (c) comprises isolating one or more bacteria whose genomes comprise a deletion in the bacterial genomic DNA between and optionally including the first and second PAM/Protospacers. Preferably, the deletion comprises the first and second PAM/Protospacers in addition to at least 1-10 kb of flanking DNA on each side of the region of DNA flanked by the first and second PAM/Protospacer sites.

Bacteria having the desired DNA deletion will easily lose the deleted DNA (between and optionally including the two CRISPR/Cas cut sites) due to the fact that it will be linear DNA and thus prone to degradation by host cell mechanisms (e.g. digested by endogenous nucleases). It is likely that the deleted section of DNA will not contain all of the essential genetic elements for stable maintenance in the cell (e.g. appropriate origin) even if it were to be re-joined before degradation.

The isolated bacteria are ones wherein the two cleaved ends of the genome have been rejoined.

In the process for removing an endogenous plasmid, step (c) comprises isolating one or more bacteria that lack the intact or uncleaved target plasmid that was previously carrying the one or more PAM/Protospacers.

The bacteria which are selected for or isolated will be live bacteria.

The invention further provides a process for making mutated bacteria, which comprises producing a deletion in a bacterial genome by a process of the invention.

In addition, the invention further provides a process for making mutated bacteria which lack target megaplasmids or other plasmids, preferably an endogenous plasmid, by a process of the invention.

In plasmids, it is possible that the method will generate a deletion that does not lead to elimination of the complete plasmid, but instead results in generation of a smaller plasmid lacking a section of DNA including the two (or more) target sites. This is more likely to be seen with larger plasmids, since they are more likely to be able to tolerate a large deletion than a smaller plasmid, as there is less chance of the deletion affecting essential elements, such as a suitable origin.

The invention also provides bacteria whose genomes have had a deletion which was produced by a process of the invention.

In addition, the invention also provides bacteria who have been caused to lose the target megaplasmid or plasmid, preferably an endogenous (mega)plasmid, by a process of the invention.

BRIEF DESCRIPTION OF THE FIGURES

FIG. 1 shows an alignment of Direct Repeat sequences from a number of clostridial species.

EXAMPLES

Example 1: Alignment of Direct Repeat Sequences from a Number of Clostridial Species Aim: To identify some Direct Repeat sequences that could be used in the process of the invention.
Method:
Direct Repeats and the Spacer sequences were found using the CRISPRFinder programme Grissa, I., Vergnaud, G., & Pourcel, C. (2007). CRISPRFinder: a web tool to identify clustered regularly interspaced short palindromic repeats. Nucleic Acids Res., 35, W52-7.
Results:
A selection of Direct Repeat sequences from a number of clostridial species are displayed in FIG. 1. In some cases the specific strain has more than one sequence so the most frequently used Direct Repeat sequence(s) is included here.

Abbreviations are as follows: C_saccharoper=*Clostridium saccharoperbutylacetonicum* N1-4 (HMT) or N1-504), C_saccharob=*Clostridium saccharobutylicum* (NCP258 or NCP262,_1 and _2 refer to the 2 main DR clusters), C_tyro=*Clostridium tyrobutyricum* (ATCC 52755, _1 and _2 refer to the 2 main DR clusters), C_pasteurianum=*Clostridium pasteurianum* (DSM 525), C_autoethanogenum=*Clostridium autoethanogenum* (DSM10061), C_sp_DLVIII=*Clostridium* sp. (DL-VIII).

Example 2: Confirming the PAM Sequence in *C. saccharoperbutylacetonicum* N1-4 (HMT)

Aim: To demonstrate how to test effectiveness of putative PAM sequences.
Method:
The sequence of Spacer_53 from the main Direct Repeat cluster of *C. saccharoperbutylacetonicum* N1-4 (HMT) was cloned into the clostridial shuttle vector, pMTL83251. Immediately adjacent to the 5' end of this Spacer Element various different trinucleotide combinations were incorporated, including the predicted PAM sequences CCC, CCG, CCT and a non-PAM sequence GAC. When correctly combined with a functional PAM sequence, the Spacer Element functions as a Protospacer.

The plasmids were transformed into *C. saccharoperbutylacetonicum* N1-4 (HMT) using standard electroporation protocols followed by an overnight recovery stage in Clostridial Growth Medium (CGM) also containing 5% glucose. The mixture was then spread onto CGM agar plates containing 5% glucose and 40 μg/ml erythromycin and left for at least 48 hours in an anaerobic cabinet at 32° C. Colonies were then counted to determine the change in transformation efficiency compared with transformation of the empty vector.

Figure 2:
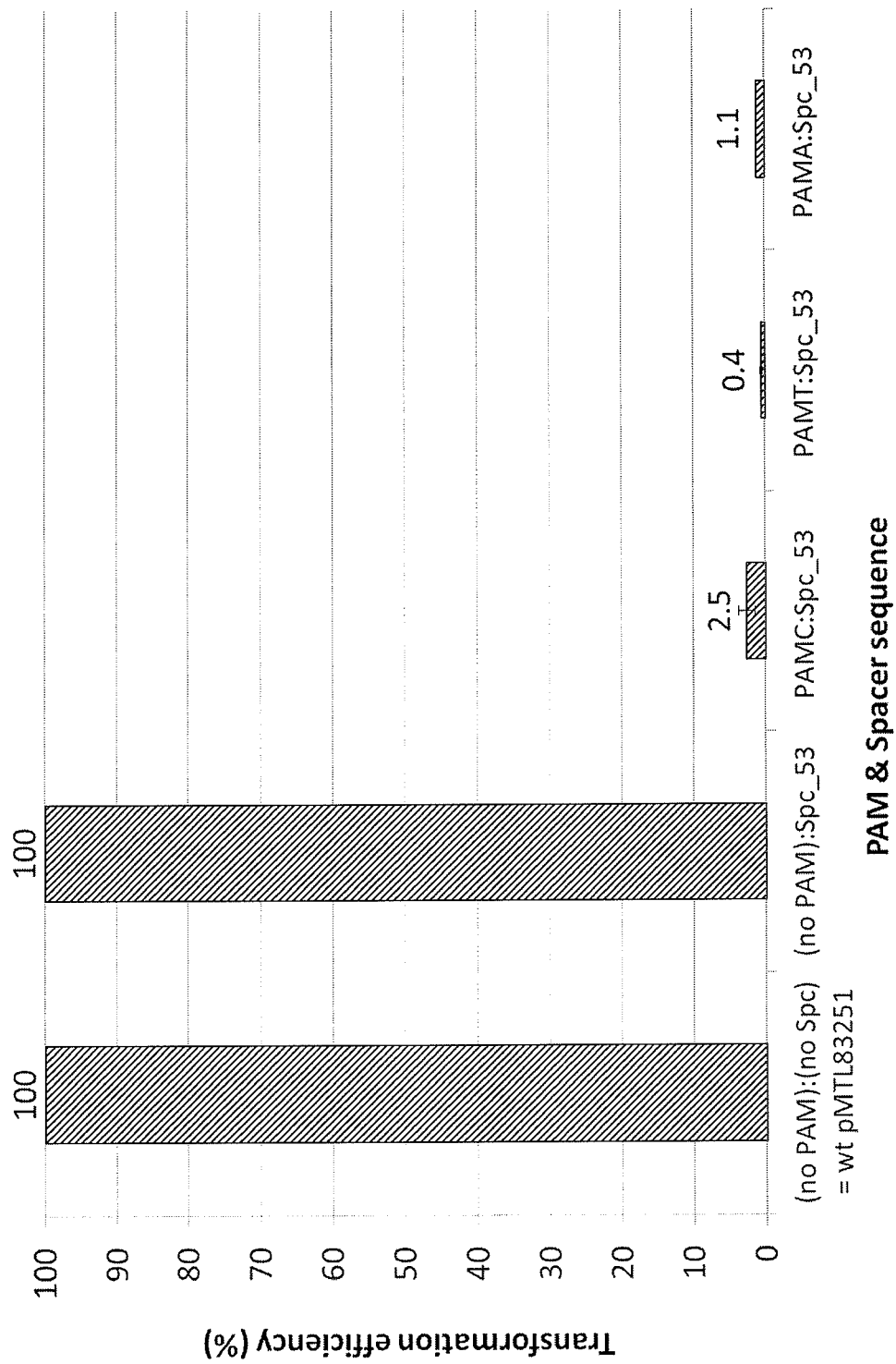
FIG. 2 shows the effect of the PAM sequence on the transformation efficiency of plasmids into *C. saccharoperbutylacetonicum* N1-4 (HMT).

CGM medium was prepared by dissolving the following amounts in 750 ml dH$_2$O: 5.0 g yeast extract, 0.75 g K$_2$HPO$_4$, 0.75 g KH$_2$PO$_4$, 0.40 g MgSO$_4$.7H$_2$O, 0.01 g FeSO$_4$.7H$_2$O, 0.01 g MnSO$_4$.4H$_2$O, 1.0 g NaCl, 2.0 g (NH$_4$)$_2$SO$_4$, 2.0 g asparagine (and 15 g bacteriological agar no. 1 if making solid medium) and autoclaved. The pH of the medium was not adjusted (usually in the region of 6.6). A 20% (w/v) glucose solution (50 g glucose dissolved in sufficient dH$_2$O to give a final volume of 250 ml) was prepared and autoclaved separately. Once cool, the glucose and CGM solutions were combined as needed.
Results:
The relative efficiencies of transformation of the different plasmids are presented in FIG. 2. Both the empty plasmid pMTL83251 and the plasmid carrying Spacer_53 without a PAM sequence gave a lawn of colonies. Plasmids carrying Spacer_53 adjacent to a 5' CCC (PAMC), CCT (PAMT) or CCA (PAMA) yielded significantly fewer colonies.

Example 3: Demonstrating the Crude Deletion Method

Aim: To show how the process of the invention can be adapted to delete a large fragment of DNA.
Method:
A selection of candidate Protospacer Elements (located immediately 3' of PAM sequences known to be functional in this bacterial system) were identified in a single target gene, and from these two were chosen that were approximately 1 kb apart (in the genomic DNA), named, for this Example, as Protospacer_1 and Protospacer_2, and being located 5' and 3' in the target gene, respectively. A Deletion Vector was designed and constructed based on a pMTL82154 backbone. It carried the leader sequence, the first Direct Repeat, Spacer_1 (corresponding to potential Protospacer_1), a second Direct Repeat, Spacer_2 (corresponding to potential Protospacer_2) and a third Direct Repeat.

This Deletion Vector was transformed into *C. saccharoperbutylacetonicum* N1-4 (HMT) using standard electroporation methods. When transformed into the cells the Deletion Vector resulted in the Cas-mediated cleavage of the gene and subsequent loss of genetic material.

Figure 3:
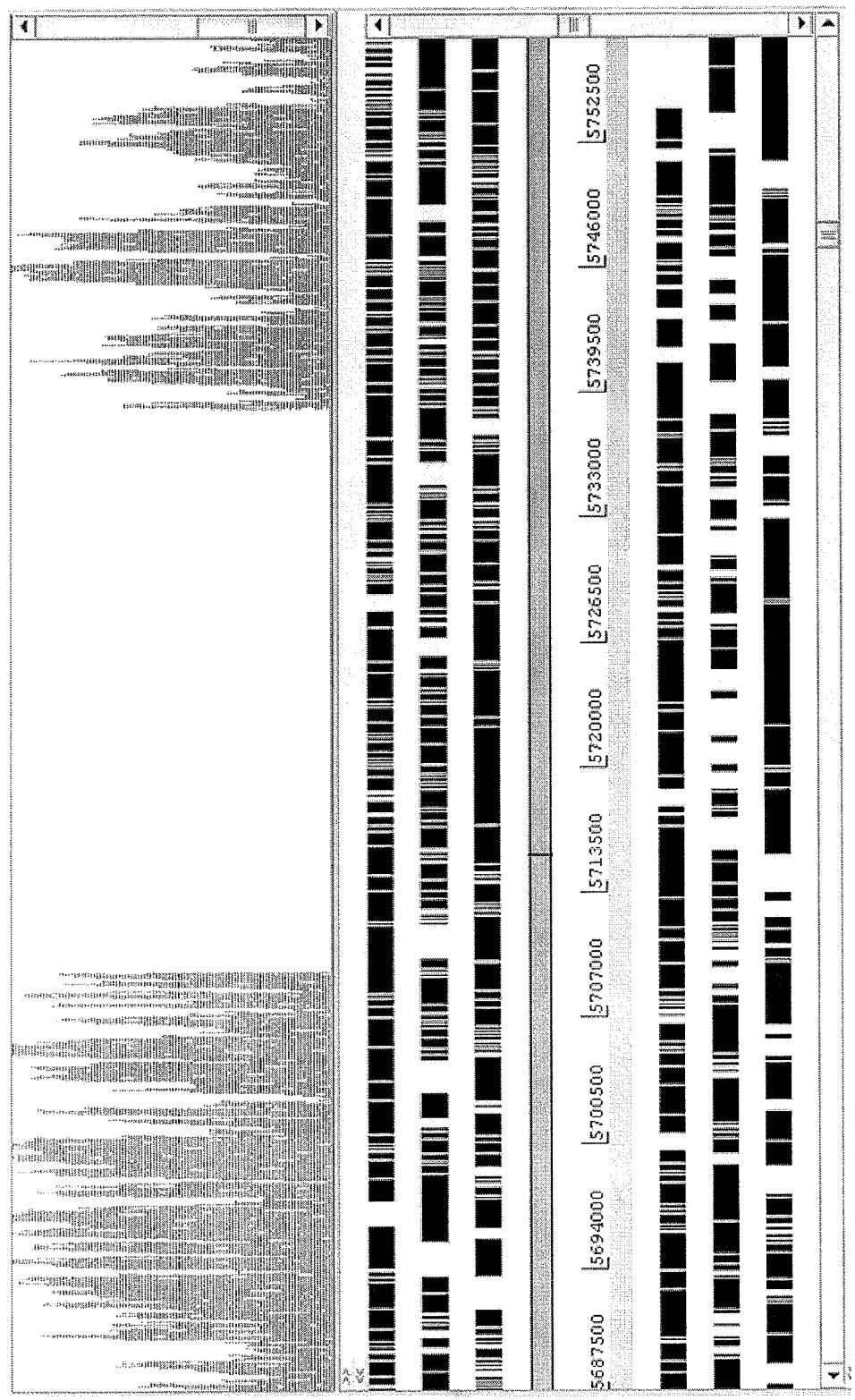
FIG. 3 compares the wild-type sequence of *C. saccharoperbutylacetonicum* N1-4 (HMT) with the same region of genomic sequence data from one of the deletion strains produced in Example 3. The diagram was prepared using Artemis genome browsing tools at: https://www.sanger.ac.uk/resources/software/artemis/.

Two colonies were recovered using this method, one of which was subsequently sequenced. This revealed that method of the invention had generated a 29205 nt deletion, compared to the parental strain. The deleted section included all of the 1 kb region between the two targeted PAM/Protospacer sites (see FIG. 3).

In the genome sequence of the mutant strain, the sequence data reading across the deletion site was as follows:

(SEQ ID NO: 12)
AAACCCTATTTCCAAAAAAATGAATGCTTTTCATGCTTTTTTAAAATTT

CTTCTATCAGCTTATTTATACAAAACTCTTCTATTTTTAGCTCATATGCT

T

The first 27 nucleotides, underlined with a wavy line, match the wildtype genome in position 5709460 to 5709486. The last 74 nucleotides, underlined with a dashed line, match the wildtype genome in position 5738692 to 5738765. The total length of the deletion was 5738692-1-5709486=29205 nt.

The invention claimed is:

1. A process for producing a deletion in a bacterial genome, wherein the bacterial genome is from a bacteria of the class Clostridia, and wherein the bacteria comprise a CRISPR/Cas system, the process comprising the steps:
   (a) transforming a population of bacteria with one or more Deletion Vectors, wherein the bacteria are of the class Clostridia and wherein the bacteria comprise a CRISPR/Cas system, and wherein the Deletion Vector(s) are capable of directing production of first and second crRNAs which target first and second PAM/Protospacers within the genomes of the bacteria within the population;
   (b) culturing the population of bacteria under conditions whereby the first and second crRNAs are produced, wherein they target the first and second PAM/Protospacers, and wherein the first and second crRNAs promote the dual cleavage of the genome in one or more bacteria within the population, and wherein the two cleaved ends of the major fragment of the bacterial genomic DNA rejoin; and
   (c) isolating one or more bacteria whose genomes comprise a deletion in the bacterial genomic DNA between the first and second PAM/Protospacers.

2. A process as claimed in claim 1, wherein one Deletion Vector is capable of directing production of both the first and second crRNAs which target the first and second PAM/Protospacers within the genomes of the bacteria within the population.

3. A process as claimed in claim 2, wherein the Deletion Vector comprises first and second Cas Spacer Elements which are flanked by Cas Direct Repeat Elements, which encode the first and second crRNAs.

4. A process as claimed in claim 3, wherein the first and second Cas Spacer Elements are in a single Cas array within the Deletion Vector or in separate Cas arrays within the Deletion Vector.

5. A process as claimed in claim 4, wherein the Deletion Vector comprises:
   (i) a Cas Leader Element,
   (ii) a first Cas Direct Repeat Element,
   (iii) a first Cas Spacer Element which is capable of directing production of the first crRNA,
   (iv) a second Cas Direct Repeat Element,
   (v) a second Cas Spacer Element which is capable of directing production of the second crRNA, and
   (vi) a third Cas Direct Repeat Element.

6. A process as claimed in claim 4, wherein the Deletion Vector comprises two arrays, the first array comprising:
   (i) a first Cas Leader Element,
   (ii) a first Cas Direct Repeat Element,
   (iii) a first Cas Spacer Element which is capable of directing production of the first crRNA,
   (iv) a second Cas Direct Repeat Element,
   and the second array comprising:
   (v) a second Cas Leader Element,
   (vi) a third Cas Direct Repeat Element,
   (vii) a second Cas Spacer Element which is capable of directing production of the second crRNA, and
   (viii) a fourth Cas Direct Repeat Element.

7. A process as claimed in claim 1, wherein a first Deletion Vector is capable of directing production of the first crRNA which targets the first PAM/Protospacers within the genomes of the bacteria within the population; and a second Deletion Vector is capable of directing production of the second crRNA which targets the second PAM/Protospacers within the genomes of the bacteria within the population.

8. A process as claimed in claim 7, wherein the first Deletion Vector comprises:
   (i) a first Cas Leader Element,
   (ii) a first Cas Direct Repeat Element,
   (iii) a first Cas Spacer Element which is capable of directing production of the first crRNA,
   (iv) a second Cas Direct Repeat Element,
   and/or the Second Deletion Vector comprises:
   (v) a second Cas Leader Element,
   (vi) a third Cas Direct Repeat Element, (vii) a second Cas Spacer Element which is capable of directing production of the second crRNA, (viii) a fourth Cas Direct Repeat Element.

9. A process as claimed in claim 1, wherein in step (b), either both of the PAM/Protospacers are removed from the bacterial genome or both of the PAM/Protospacers are rendered incapable of being recognised by crRNAs which recognise the PAM/Protospacers.

10. A process as claimed in claim 1, wherein the bacteria have an endogenous CRISPR/Cas system.

11. A process as claimed in claim 1, wherein the bacteria have a Type I CRISPR/Cas system.

12. A process as claimed in claim 1, wherein the bacteria are of the genus *Clostridium*.

13. A process as claimed in claim 12, wherein the bacteria is selected from the group consisting of *C. acetobutylicum, C. arbusti, C. aurantibutyricum, C. beijerinckii, C. cellulovorans, C. cellulolyticum, C. thermocellum, C. thermobutyricum, C. pasteurianum, C. kluyveri, C. novyi, C. saccharobutylicum, C. thermosuccinogenes, C. thermopalmarium, C. saccharolyticum, C. saccharoperbutylacetonicum, C. tyrobutyricum, C. tetanomorphum, C. magnum, C. ljungdahlii, C. autoethanogenum, C. butyricum, C. puniceum, C. diolis, C. homopropionicum* and *C. roseum*.

14. A process for making a mutated bacterium, wherein the bacterium is of the class Clostridia, the process comprising producing a deletion in a bacterial genome, wherein the bacterial genome is from a bacteria of the class Clostridia, by a process as claimed in claim 1.

* * * * *